(12) United States Patent
Chaiken et al.

(10) Patent No.: US 11,415,511 B2
(45) Date of Patent: *Aug. 16, 2022

(54) DETERMINATION OF TURBIDITY USING ELASTICALLY AND INELASTICALLY SCATTERED LIGHT

(71) Applicant: Syracuse University, Syracuse, NY (US)

(72) Inventors: Joseph Chaiken, Fayetteville, NY (US); Jerry Goodisman, Syracuse, NY (US)

(73) Assignee: Syracuse University, Syracuse, NY (US)

( * ) Notice: Subject to any disclaimer, the term of this patent is extended or adjusted under 35 U.S.C. 154(b) by 536 days.

This patent is subject to a terminal disclaimer.

(21) Appl. No.: 15/695,289

(22) Filed: Sep. 5, 2017

(65) Prior Publication Data

US 2018/0011017 A1    Jan. 11, 2018

Related U.S. Application Data

(63) Continuation of application No. 14/027,804, filed on Sep. 16, 2013, now abandoned, which is a continuation-in-part of application No. 12/889,396, filed on Sep. 23, 2010, now Pat. No. 8,538,499.

(60) Provisional application No. 61/245,020, filed on Sep. 23, 2009.

(51) Int. Cl.
| | |
|---|---|
| *G01N 21/49* | (2006.01) |
| *G01N 21/64* | (2006.01) |
| *A61B 5/145* | (2006.01) |
| *A61B 5/1455* | (2006.01) |

(52) U.S. Cl.
CPC .......... *G01N 21/49* (2013.01); *A61B 5/1455* (2013.01); *A61B 5/14535* (2013.01); *G01N 21/6486* (2013.01); *A61B 5/14532* (2013.01)

(58) Field of Classification Search
None
See application file for complete search history.

(56) References Cited

PUBLICATIONS

Renuka, R., S. Ramamurthy, and L. Srinivasan. "Interaction of zincate with additives turbidimetric, IR and Raman spectral analyses." Journal of power sources 89.1 (2000): 70-79.*

* cited by examiner

*Primary Examiner* — G Steven Vanni
(74) *Attorney, Agent, or Firm* — Bond Schoeneck and King PLLC; David Nocilly

(57) ABSTRACT

The invention provides a method of determining turbidity and concentration simultaneously a sample by irradiating the sample with a single incident wavelength and simultaneously measuring wavelength shifted (IE) and unshifted (EE) light emitted. A relative volume of light emitted from two phases may be determined, wherein the two phases comprise a first Rayleigh and Mie scattering and fluorescent phase associated with suspended particles, and a second, non-scattering but fluorescent phase associated with suspending solution. Volumes of the phases and/or concentrations of specific fluorophores or Raman active species are calculated from the volume of light emitted by the first phase relative to the total volume of light emitted from the first and second phases.

6 Claims, 10 Drawing Sheets

DETERMINATION OF TURBIDITY USING ELASTICALLY AND INELASTICALLY SCATTERED LIGHT

CROSS-REFERENCE TO RELATED APPLICATIONS

This application is a continuation of U.S. application Ser. No. 14/027,804, filed on Sep. 16, 2013, which was a continuation-in-part of U.S. application Ser. No. 12/889,396, filed on Sep. 23, 2010, which claims the benefit of U.S. Provisional Application No. 61/245,020, filed on Sep. 23, 2009, both of which are hereby incorporated by reference in their entireties.

BACKGROUND OF THE INVENTION

1. Field of the Invention

The present invention relates to the measurement of suspended matter in a solution and, more particularity, to the measurement of turbidity in an in vitro sample.

2. Description of the Related Art

Algal biofuel production is a process that has received much attention as a more environmentally friendly renewable energy source. The algae growth starts with proliferation where the cells multiply and ends with profusion by the production of fats which can be generated into biofuels. The growth of the algae culture is currently determined by removing an aliquot, which could potentially contaminate the culture. Accordingly, there is a need for a way to non-invasively measure the amount of suspended material in a sample.

BRIEF SUMMARY OF THE INVENTION

The present invention provides a method of determining turbidity in an in vitro sample. The method comprises irradiating a sample with a single incident wavelength and simultaneously measuring wavelength shifted (IE) and unshifted (EE) light emitted from the sample. The method further comprises determining a relative volume of light emitted from two phases, wherein the two phases comprise a first Rayleigh and Mie scattering and fluorescent phase associated with suspended particles, and a second, non-scattering phase associated with the supporting solution. As an example, the apparatus and algorithms disclosed in the parent application measure hematocrit (Hct) and plasma volume (Op) noninvasively in the blood in vivo and are thus being applied to measuring turbidity in in vitro sample using the apparatus and algorithms with or without some minor modifications.

In a typical embodiment, the incident wavelength is 280-2500 nm. In some embodiments, the incident wavelength is 785, 805 or 830 nm. The measuring is typically at 500-1800 $cm^{-1}$ for Stokes shifted light, and at $-30-+10$ $cm^{-1}$ for unshifted light.

In one embodiment, the determining comprises calculating the turbidity as:

$$\phi_r / (\phi_r + \phi_p) \quad [5]$$

$$\text{wherein } \phi_r = a + \left(b \frac{EE}{EE_0}\right) + \left(c \frac{IE}{IE_0}\right) \quad [8]$$

$$\phi_p = d + \left(e \frac{EE}{EE_0}\right) + \left(f \frac{IE}{IE_0}\right) \quad [9]$$

$$EE = \aleph_1 + \aleph_2 \phi_p + \aleph_3 \phi_r \quad [6]$$

$$IE = \aleph_4 + \aleph_5 \phi_p + \aleph_6 \phi_r \quad [7]$$

and wherein EE is total elastically (unshifted) emitted light, IE is total inelastically (shifted) emitted light, $\aleph_1$ and $\aleph_4$ are the fractions of EE and IE, respectively, from static tissue; $\aleph_2$ and $\aleph_5$ are the fractions of EE and IE, respectively, from suspended particles, such a blood cells; $\aleph_3$ and $\aleph_6$ are the fractions of EE and IE, respectively, from the supporting fluid, such as plasma; and $\aleph_{1-6}$ are calculated numerically using the radiative transport equation (RTE) using optical and geometric parameters appropriate to the tissue and instrumentation appropriate to the specific probing, to determine EE and IE as a function of $\phi_r$ and $\phi_p$; wherein $EE_o$ and $IE_o$ are calculated or measured average values of EE and IE over a calibration time period that depends on the laser power and volume of tissue probed under a reference condition. Values for a-f can be obtained by inverting equations [6] and [7] to express $\phi_r$ and $\phi_p$ in terms of EE and IE.

The invention provides an apparatus for measuring turbidity in a sample. The apparatus comprises a means for irradiating the sample with a single incident wavelength; a means for simultaneously measuring wavelength shifted and unshifted light emitted from the sample; and means for determining a relative volume of light emitted from two phases, wherein the two phases comprise a first predominantly Rayleigh and Mie scattering and fluorescent phase associated with suspended particles, and a second, non-scattering fluorescent phase associated with the fluid medium. Typically, the apparatus also includes means for calculating a volume fraction of suspended particles relative to the total volume of suspended parties and fluid medium.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 8:
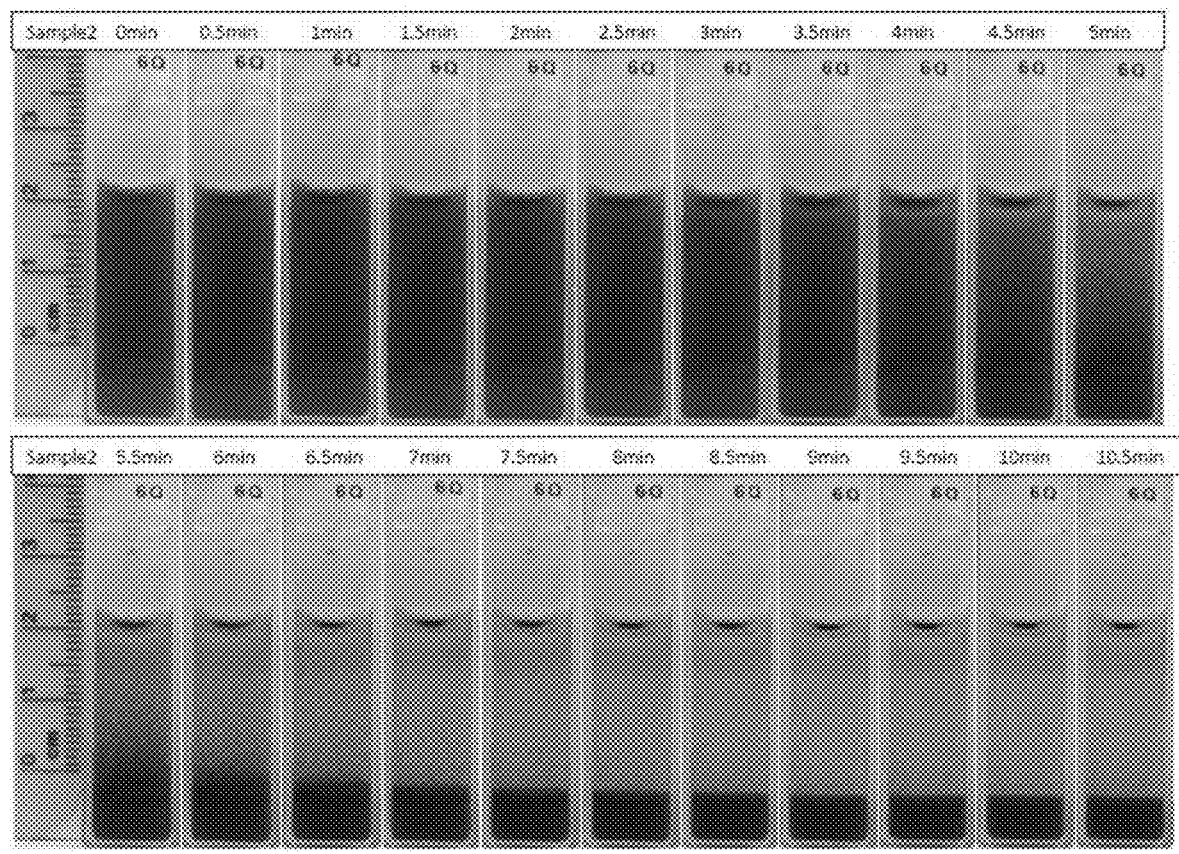
Figure 9:
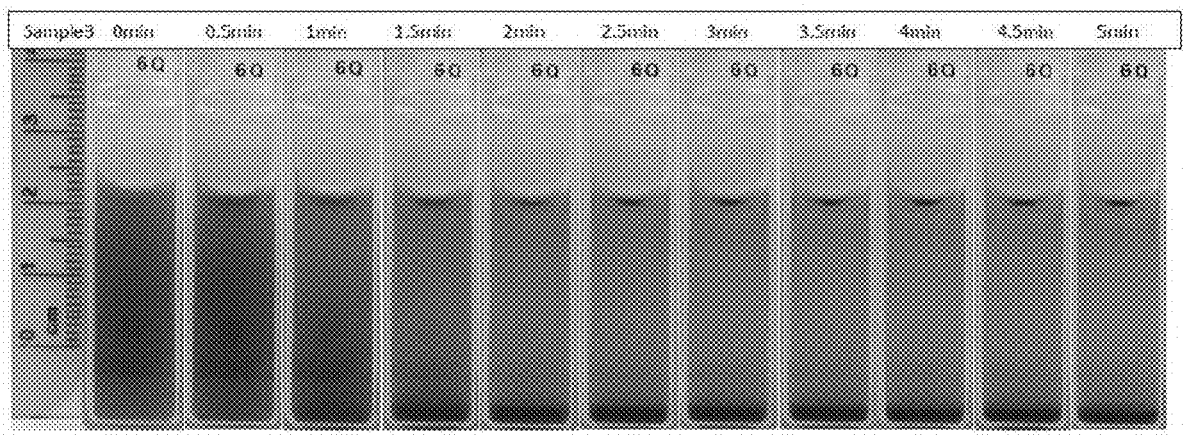
Figure 10:
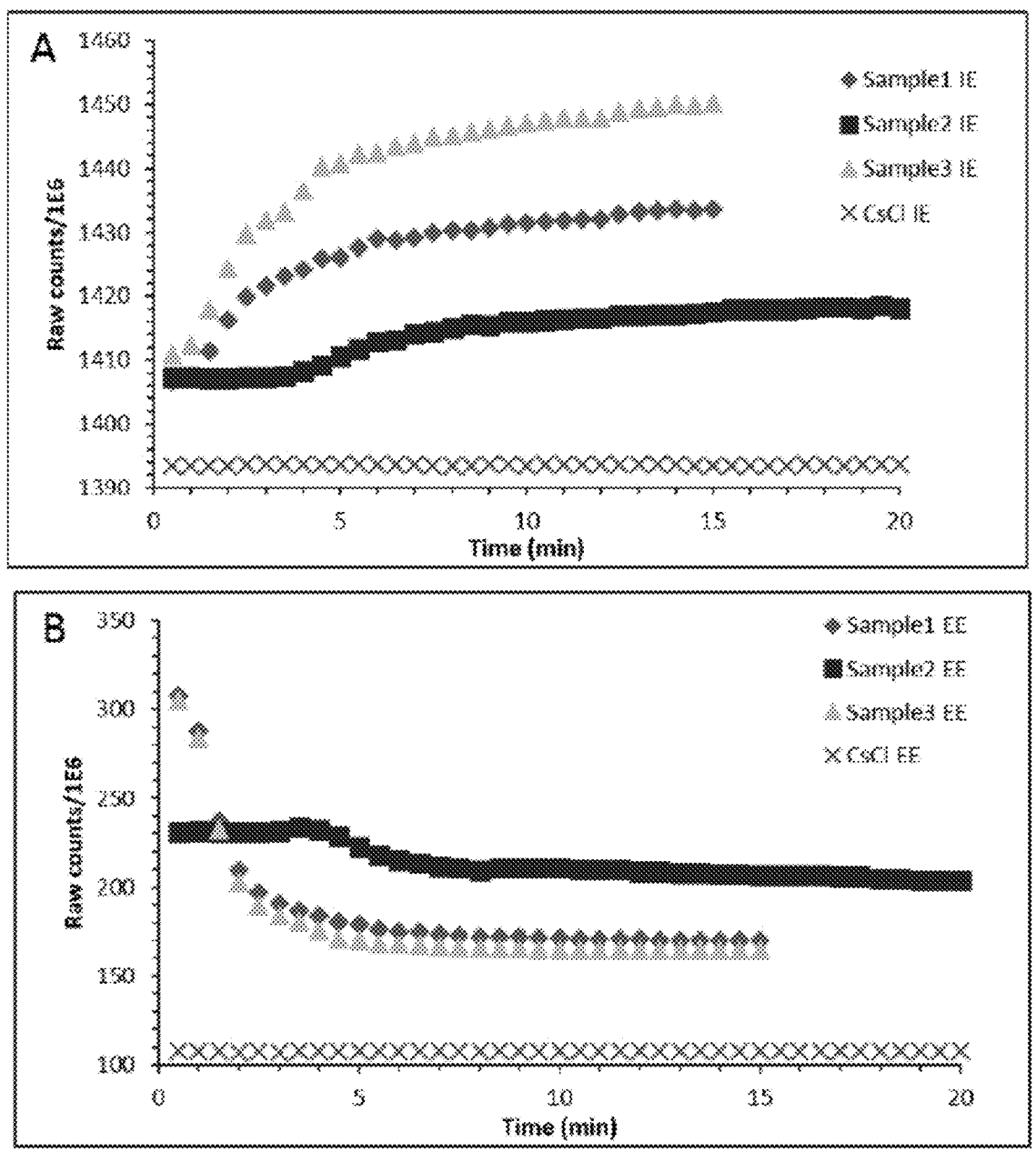
Figure 11:
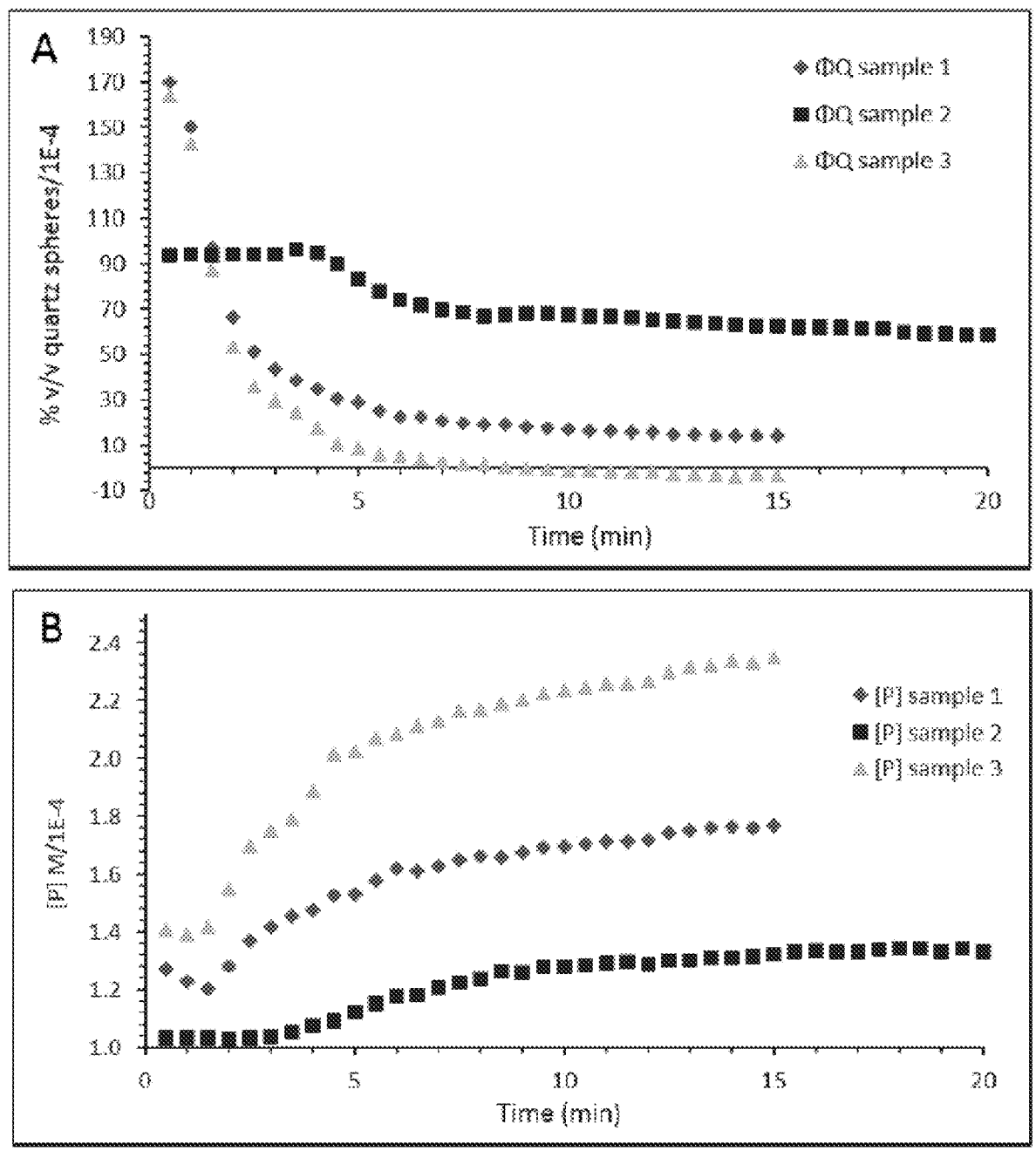

FIG. 8 is a series of images of sample 2 quartz spheres settling with 0.00185% v/v spheres and 9.92E$^{-5}$ M porphyrin FIG. 9 is a series sample 3 quartz spheres settling with 0.0111% v/v spheres and 1.488E$^{-4}$ M porphyrin;

FIG. 10 is a series of graphs showing A) IE and B) EE measurements over time as the quartz spheres settle out of the probed region;

FIG. 11 is a series of graphs showing calculated A) $\Box$Q and B) [P] over time as the quartz spheres settled out of the probed region.

DETAILED DESCRIPTION OF THE INVENTION

Referring now to the drawings, wherein like reference numerals refer to like parts throughout, the present invention comprises the apparatus and algorithm of U.S. application Ser. No. 12/889,396, hereby incorporated by reference, which was used to accurately determine hematocrit in vivo. The apparatus and algorithm of present invention may also be used to evaluate certain in vitro measurements, such as turbidity.

The present invention involves apparatus and a mathematical algorithm to take measurements produced by the apparatus and report the relative fractions of two phases present in a system. The phases are distinguished by differing indices of refraction, densities, light absorption and emission characteristics and chemical constitution. The apparatus includes a laser that shines one color into a sample as well as optics to collect the light that is remitted by the sample. Preferably, the apparatus of the present invention comprises a source for delivering an incident wavelength of about 280-2500 nm. In some embodiments, the incident wavelength may be 405, 450, 632, 670, 785, 805 830, or 940 nm. The collected light must be separated into two parts, one part having the same color as the incident laser and the other having a different color. Thus, the optics detector must be capable of measuring at about 500-1800 cm$^{-1}$ for shifted light, and at about −30-+10 cm$^{-1}$ for unshifted light. The basic principle is that the amount of same color emitted light is strongly affected by the presence of physical objects that scatter the light without changing color and the amount of color shifted light produced depends on the presence of some chemical species and spectroscopic processes that depend on the internal energy levels of one or more molecules.

Data may be obtained using highly polarized, external cavity diode lasers (depending on specific purposes, either Process Instruments, Salt Lake, Utah, USA or Sacher Lasertechnik Tiger Model, Marburg, Germany) with clean-up and edge filters (Semrock, Rochester, N.Y., USA). Data shown below corresponds to 830 nm and 200 mW excitation. Because the laser light is propagated with an angle of incidence of 53±1° (the uncertainty is the practical limit and not a precisely known number) to the normal to the plane of the aperture, the laser cross-section on the finger is observed to be elliptical. Using knife edge scanning experiments and Zap-it paper, it is estimated that the elliptical spot has a 100 µm minor axis and a 237 µm major axis. The spectrograph (Process Instruments, Salt Lake, Utah, USA) is fiber-coupled to a collection train consisting of a custom triplet collection lens, followed by a (Semrock Razor Edge) filter to remove the laser line, and then a refocusing lens. The 59-fiber bundle presents an AR coated circular target to the refocusing lens and a line configuration at the spectrograph entrance slit. The effective slit width is 70 µm and the net collection and spectrograph system is approximately f/2. The wavelength-dispersed light is imaged onto either an Andor DU420-BR-DD CCD camera operating at 65° C. or a Critical Link MityCCD-E3011-BI CCD camera, cooled to −45° C.

Because both shifted and unshifted light can be collected simultaneously, two pieces of independent information are obtained about the sample. There are two equations in the algorithm from classical radiation transfer theory that relate the presence of the two phases to the two pieces of information. As a result, the invention includes two independent equations having two variables that are inverted to give the two volume fractions for the two phases. Knowledge of the two volume fractions constitutes the end product of the invention, which can in turn be used to accomplish many useful tasks, such as measuring hemocrit in vivo or turbidity in an in vitro sample.

The algorithm of the present invention comprises calculating the turbidity as:

$$\phi_r / (\phi_r + \phi_p) \quad [5]$$

$$\text{wherein } \phi_r = a + \left(b \frac{EE}{EE_0}\right) + \left(c \frac{IE}{IE_0}\right) \quad [8]$$

$$\phi_p = d + \left(e \frac{EE}{EE_0}\right) + \left(f \frac{IE}{IE_0}\right) \quad [9]$$

$$EE = \aleph_1 + \aleph_2 \phi_p + \aleph_3 \phi_r \quad [6]$$

$$IE = \aleph_4 + \aleph_5 \phi_p + \aleph_6 \phi_r \quad [7]$$

and wherein EE is total elastically (unshifted) emitted light, IE is total inelastically (shifted) emitted light, $\aleph_1$ and $\aleph_4$ are the fractions of EE and IE, respectively, from static tissue; $\aleph_2$ and $\aleph_5$ are the fractions of EE and IE, respectively, from suspended particles, such as red blood cells; $\aleph_3$ and $\aleph_6$ are the fractions of EE and IE, respectively, from the supporting fluid, such as plasma; and $\aleph_{1-6}$ are calculated numerically using the radiative transport equation (RTE) using optical and geometric parameters appropriate to the tissue and instrumentation appropriate to the specific probing, to determine EE and IE as a function of $\phi_r$ and $\phi_p$; wherein $EE_o$ and $IE_o$ are calculated or measured average values of EE and IE over a calibration time period that depends on the laser power and volume of sample probed under a reference condition. Values for a-f can be obtained by inverting equations [6] and [7] to express $\phi_r$ and $\phi_p$ in terms of EE and IE.

Figure 1:
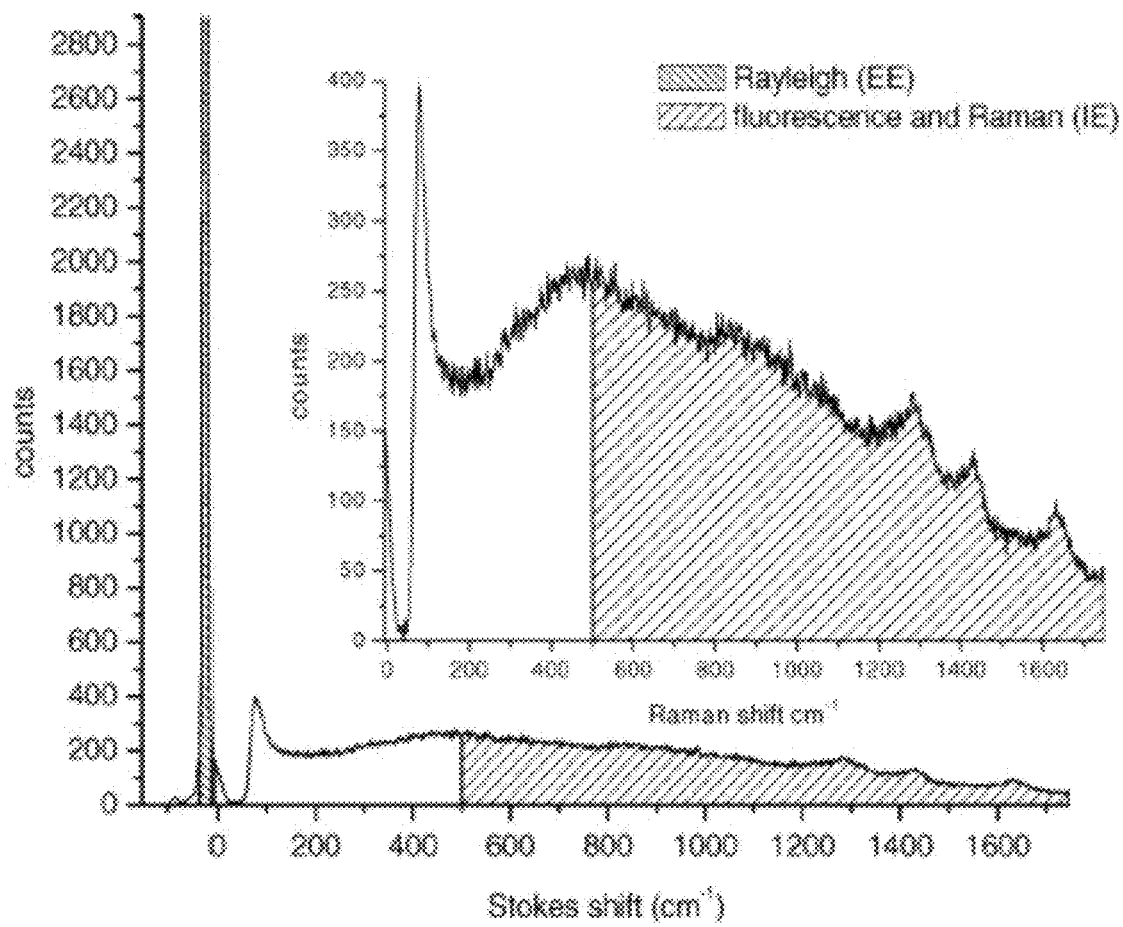
FIG. 1 is a graph of intensity verses frequency showing the EE and IE regions regions.

As seen in FIG. 1, Raman spectroscopy measures the change in energy between light entering the sample and the light that is emitted. Light emitted with the same energy is elastically scattered (EE) whereas light emitted with a different energy is inelastically scattered (IE). The EE and IE can be analyzed as independent simultaneous measurements due to being caused by fundamentally different processes. FIG. 1 demonstrates a typical spectrum and defines the regions of the spectrum corresponding to EE and IE.

In U.S. application Ser. No. 12/889,396, the present invention was used to determine hemocrit based on the intensity of scattered radiation from all three phases that is detected outside the skin, given volume fractions, absorption coefficients, and scattering coefficients for the three phases. The present invention also accounts for the variation in detected intensity with geometric parameters (placement of source and detector, etc.) and changes in volume fractions.

For example, based on experiences with a range of actual skin types and a specific experimental apparatus, for the base calculation, geometric parameters are used as follows: The dome formed when the fingertip is brought into registration with the 0.21 mm diameter optical aperture is assumed to be a spherical cap with radius 0.1 cm and height 0.005 cm. The origin of coordinates is in the center, 0.005 cm below the top of the dome. The angle between the direction of the incoming beam and the vertical is 0.980 radians, and the origin of the beam is chosen so that the center of the beam crosses the skin surface at the top of the dome (actually at x=0.0025404 cm, y=0.004997 cm). The detector center is at x=0.015 cm, y=0.013 cm.

The values of the parameters characterizing the skin for the simulations are given in Tables 1 and 2. The parameters used in calibrating the algorithm in this description are given in Table 3 and are somewhat different from those in Table 2. The differences were based on the original authors' indications of the effect of isolating the tissues from their normal in vivo setting and were needed to obtain agreement with empirical observations. It should not be assumed that the parameters given are necessarily optimized.

The volume fractions in Table 1 are based on estimates of the average capillary density, dimensions and a hematocrit of 0.10 for the blood in the most vascularized second layer. The third layer was given 10% of the total blood fraction of the second layer, i.e. from the top of the capillary loops down to the superficial dermal plexus, consistent with medium to deep dermis. The calculations show that, for all three phases, the contribution of layer c is much less than that of layers a and b, so that the assumptions made for layer c are not critical. Even if the total blood fraction is assumed to be as high as 0.05, the scattering length is very long compared with the dimensions of the layers and the single scattering limit is appropriate. For the calibration of the algorithm given below, volume fractions used were consistent Jacques' estimates for well perfused skin, as would be appropriate to fingertips. The estimates in Table 1 are more appropriate of forearm skin.

TABLE 1

Assumed volume fractions of the three phases in the three layers

| Phase | Layer a | Layer b | Layer c |
| --- | --- | --- | --- |
| p = plasma | 0.00 | 0.0072 | 0.001200 |
| r = red blood cells | 0.00 | 0.0008 | 0.000133 |
| t = static tissue | 1.00 | 0.9920 | 0.998667 |

TABLE 2

Absorption and scattering coefficients for the three phases

| Phase | Absorption coefficient | Elastic (Rayleigh) scattering coefficient | Inelastic (fluorescence) scattering coefficient |
| --- | --- | --- | --- |
| r = rbc | $\alpha_r = 4.5$ cm$^{-1}$ | $\mu_r = 300$ cm$^{-1}$ | 4.5 cm$^{-1}$ |
| p = plasma | $\alpha_p = 0.3$ cm$^{-1}$ | $\mu_p = 0.60$ cm$^{-1}$ | 0.30 cm$^{-1}$ |
| t = static tissue | $\alpha_t = 5$ cm$^{-1}$ | $\mu_t = 12$ cm$^{-1}$ | 5 cm$^{-1}$ |

In the present invention, the sum of the absorption and inelastic scattering coefficients, weighted by phase volume fractions, are added to give the attenuation coefficient for each layer. The calculated elastic scattering intensity from each phase is proportional to the corresponding elastic scattering coefficient, and the inelastic scattering intensity is proportional to the inelastic scattering coefficient times a quantum yield. The volume fractions (see Table 1) add up to unity, implying that there are no voids.

This is summarized in equations [1] and [2] using $\phi$ for each of the volume fractions, i.e. RBCs, plasma and static tissue.

$$1 = \phi_r + \phi_p + \phi_s \quad [1]$$

$$0 = d\phi_r + d\phi_p + d\phi_s \quad [2]$$

Good agreement between theory and experiment was obtained by summing the contributions from each phase and each layer. Obviously, one can measure only the total elastic and inelastic scattering, but one can calculate the separate contributions, as shown below. It is clear that, because of the increased path length and attenuation, the contribution of layer c is unimportant. The calculations show that the scattering from any phase is a linear function of the volume fraction of that phase in layer b. Thus, it is the blood volume fractions in layer b that are measured; the hematocrit involves volume fractions in layer b.

$$Hct = \phi_r / (\phi_r + \phi_p) \quad [3]$$

Based on the results of many calculations with the model, it is assumed that the observed elastic and inelastic scattering intensities are linear functions of the volume fractions of the three phases in layer b. Using [1], one may write this as $$EE = + \aleph_1 + \aleph_2 \phi_p + \aleph_3 \phi_r \quad [4]$$

$$IE = + \aleph_4 + \aleph_5 \phi_p + \aleph_6 \phi_r \quad [5]$$

The linear dependence is both direct (the amount of scattering from any phase at any point is proportional to the volume fraction of that phase at that point) and indirect (the scattering is proportional to the incident light intensity, which is determined by the attenuation, and the light reaching the detector is attenuated as well). It is important to note that the observed values of EE and IE depend on how they are measured and geometrical parameters of the system. In particular, the yield of measured scattered photons depends on the probed volume, the frequency range considered, and the incident laser flux. However, relations between the first three $\aleph_s$ and relations between the second three $\aleph_s$ can be obtained from the model calculations.

A series of calculations using the model were performed to obtain elastic and inelastic scattering with values of $\phi_r$ and $\phi_p$ centered around 0.004 and 0.036 respectively. ($\mu_r$=25, $\alpha_r$=150, quantum yield=1E-5). It was verified that both calculated elastic and calculated inelastic scatterings were linear in the volume fractions ($r^2 \geq 0.999$). The best bilinear fits were (C indicates calculated quantities):

$$EC=0.0.313583-0.108563\phi_r+0.045209\phi_p$$

$$IC=(0.631030+14.83102\phi_r+0.263197\phi_p)\times 10^{-5}$$

Since EE is proportional to EC and IE is proportional to IC, the ratios of $\aleph_2$ and $\aleph_3$ to $\aleph_1$, and the ratios of $\aleph_5$ and $\aleph_6$ to $\aleph_4$ are now known. One can thus write;

$$EE=\aleph_1(1+0.144427346202\phi_p-0.346202\phi_r) \quad [6]$$

$$IE=\aleph_4(1-2.298501\phi_p+20.889993\phi_r) \quad [7]$$

And that leaves only two parameters to be determined. These are essentially normalizing parameters. Since the calculations refer to $\phi_r=0.0040$ and $\phi_p=0.0360$, $\aleph_1=EE_0/1.003815$ and $\aleph_4=IE_0/1.000814$, where $EE_0$ and $IE_0$ are measured at some reference point with respect to the measurement conditions, i.e. a particular applied pressure relative to the test subject's diastolic and systolic blood pressures or perhaps a particular temporal position with respect to the cardiac pulse. Any choice should be based on measurement conditions that actually produce the assumed set of volume fractions defining the model calculation.

Solving [6] and [7] for the volume fractions gives $$\phi_r = 1.034740\left(1.003815\frac{EE}{EE_0}-1\right)+0.065018\left(1.00814\frac{IE}{IE_0}-1\right) \quad [8]$$

$$\phi_p = 9.404260\left(1.003815\frac{EE}{EE_0}-1\right)+0.1558538\left(1.00814\frac{IE}{IE_0}-1\right) \quad [9]$$

The Hct is then given by [3]. Note that if $IE=IE_0$ and $EE=EE_0$ these equations yield $\phi_r=0.0040$, $\phi_p=0.0360$. Thus one can calculate the two volume fractions, $\phi_r$ and $\phi_p$, from measured quantities, and then obtain the hematocrit.

Figure 2:
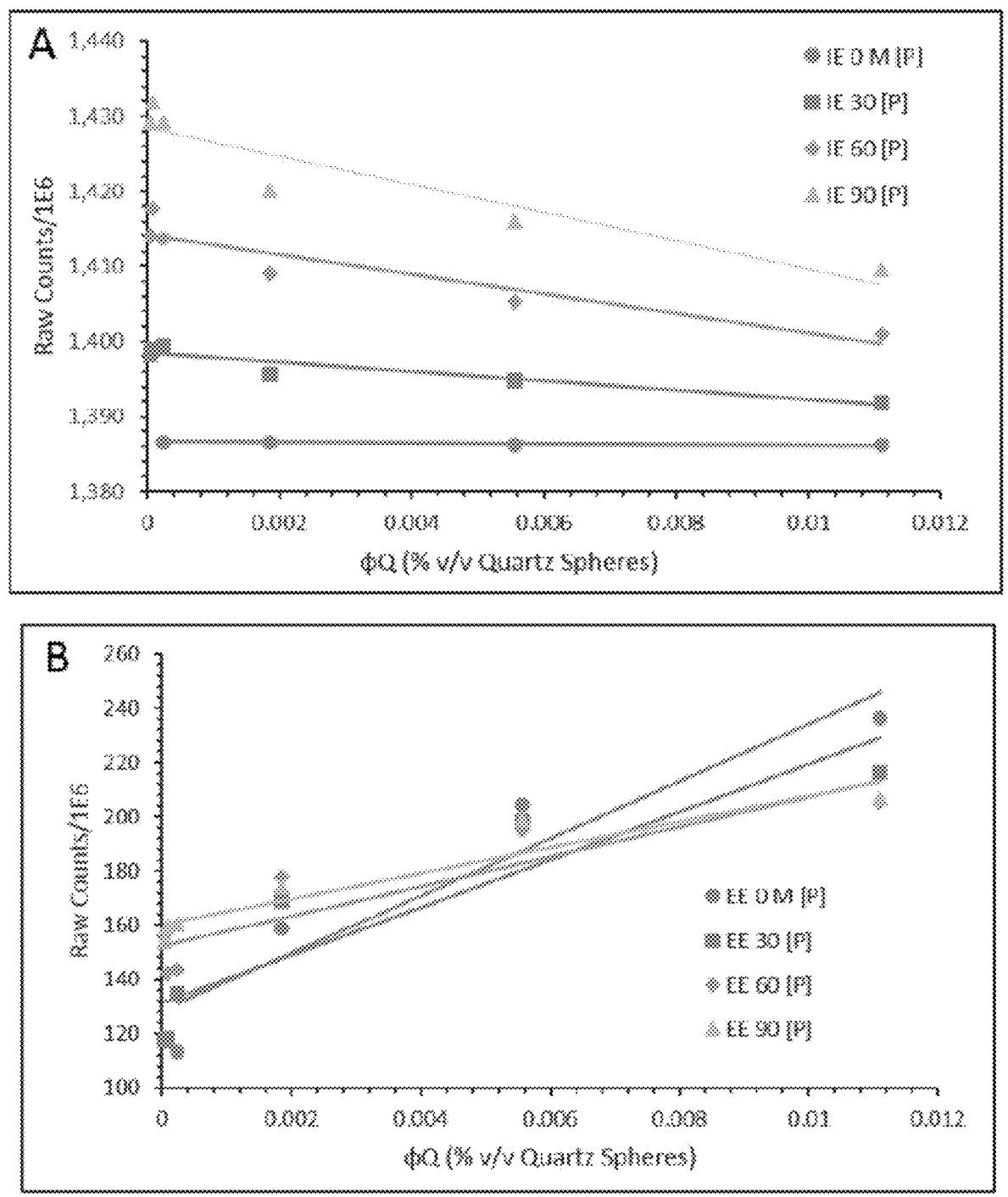
FIG. 2 is a series of graphs showing the linear relationship with respect to quarts spheres in an Example of the present invention.

In the Example below, this algorithm is being applied to quartz spheres suspended in a porphyrin solution in aqueous CsCll for adjustable density, and in a particular experimental arrangement that by its nature produces a background signal The in vitro experiment was designed with varying concentrations of both quartz spheres and porphyrin, keeping a constant volume for each sample. It is important for both variables i.e. the $\phi_p$ and $\phi_r$ or their analogues to demonstrate a linear relationship with respect to both EE and IE to fit the data. FIG. 2 displays the linear relationship with respect to quarts spheres and FIG. 3 the relationship with respect to porphyrin.

Having demonstrated linear relationships with respect to IE and EE for both variables independently, the system can be fitted to the hematocrit algorithm yielding equations [8] and [9], $$ch=a+b(EE)+c(IE) \quad [8]$$

$$[P]=d+e(EE)+f(IE) \quad [9]$$

where OQ is the volume fraction of quartz spheres and [P] is the concentration of porphyrin in molarity. Since the total volume in this case is the focal volume of the laser inside the fluid in the cuvette, the volume fraction of the quartz determines the volume fraction of the remaining fluid phase. However, the fluorescence and Raman emission produced by the fluid phase is a function of the concentration of any fluorophores or Raman active species thereby by providing the other independent variable needed to characterize the IE in this intentionally turbid system. Thus a volume fraction of the fluid phase can be replaced with the concentration of the active species and the units will be reflected in the units of the parameters a-f. Thus with appropriate choices the closure relations analogous to equations 1 and 2 are implicitly satisfied in this in vitro analogue.

These only serve as constraints to be satisfied when optimizing the parameters a-f for the in vivo system. For the Hct measurement i.e. the in vivo system there is homeostasis that defines the $EE_0$ and $IE_0$ however, this is not the case for the present experiment. Thus, equations [8] and [9] only utilize the raw measurements of both EE and IE. The only requirement for the algorithm to be applicable is for the IE and EE to be linearly independent measurements because a two equation system in two unknowns can always be inverted.

Figure 3:
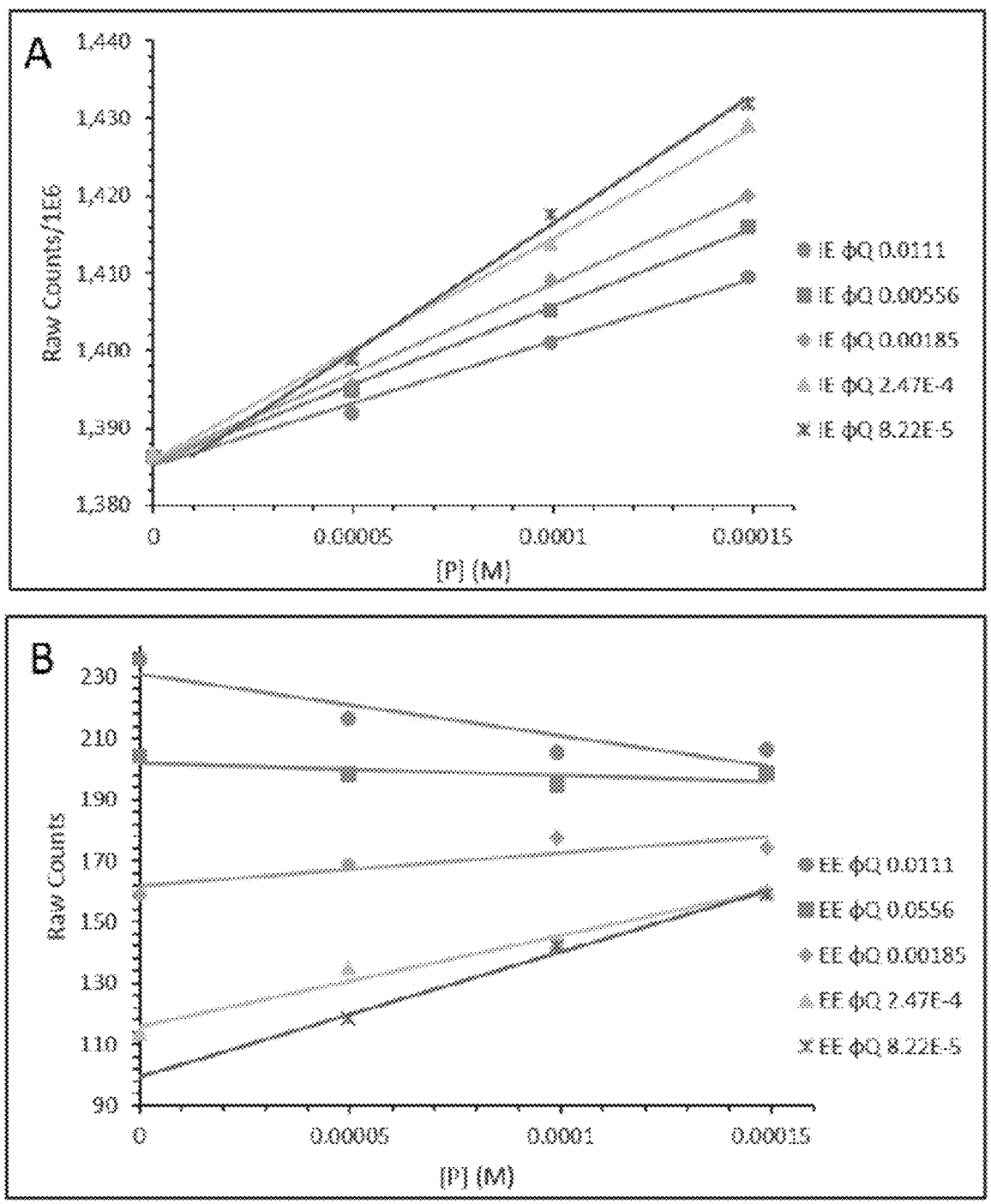
FIG. 3 is a series of graphs showing the relationship with respect to porphyrin in an Example of the present invention.

As in the hematocrit algorithm, the parameters a-f can be calculated based on a fit of the experimental data comprising FIGS. 2 and 3. To calculate a-c, a bilinear fit was applied with OQ as the dependent variable and EE and IE as independent variables. For d-f, [P] was the dependent variable keeping EE and IE as independent variables. The calculated parameters are introduced into equations [8] and [9] yielding equations [10] and [11].

$$\phi_Q=0.0897+9.89413E^{-11}(EE)-7.33145E^{-11}(IE) \quad [10]$$

$$[P]=-0.001501+3.34025E^{-13}(EE)+3.57857E^{-12}(IE) \quad [11]$$

Figure 4:
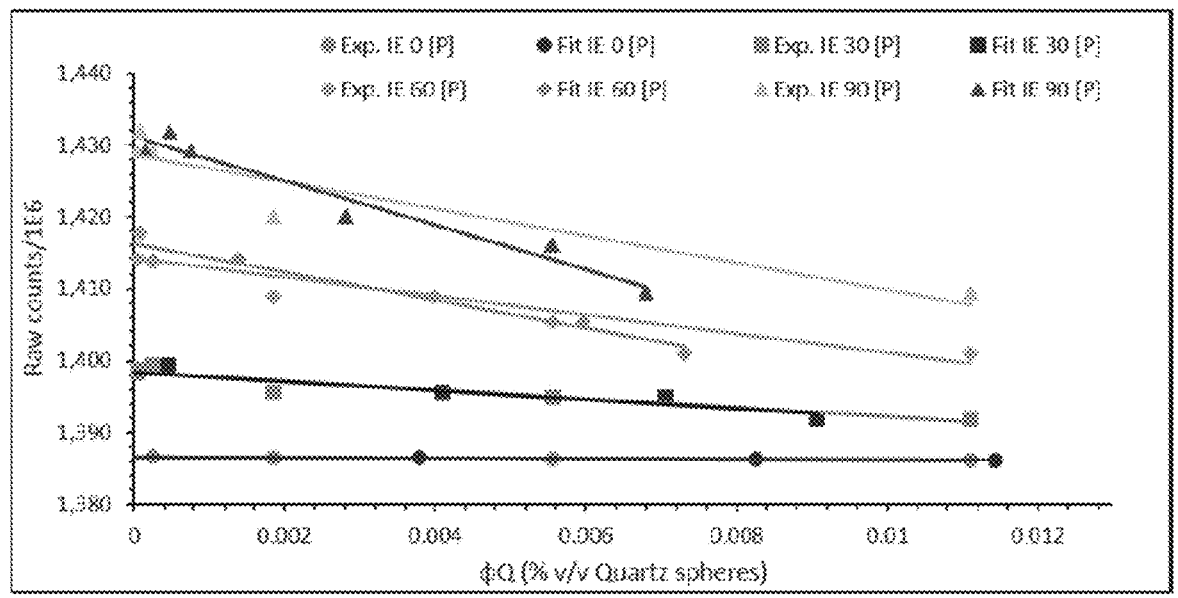
FIG. 4 is a graph showing IE dependence on the volume fraction of quartz spheres at various concentrations of porphyrin and the fit [P] and $\phi_Q$ are compared to the expected values from FIGS. 2 and 3.
Figure 5:
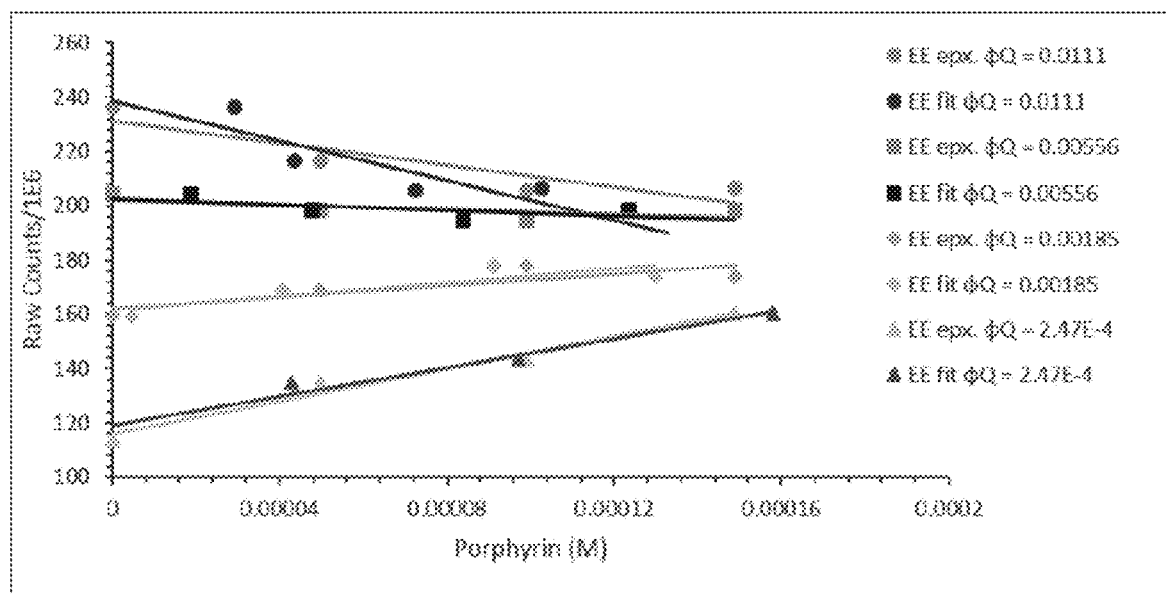
FIG. 5 is a graphs showing EE dependence on the concentration of porphyrin at various volume fractions of quartz spheres with the expected values compared to the fitted values calculated from equations [10] and [11]
Figure 6:
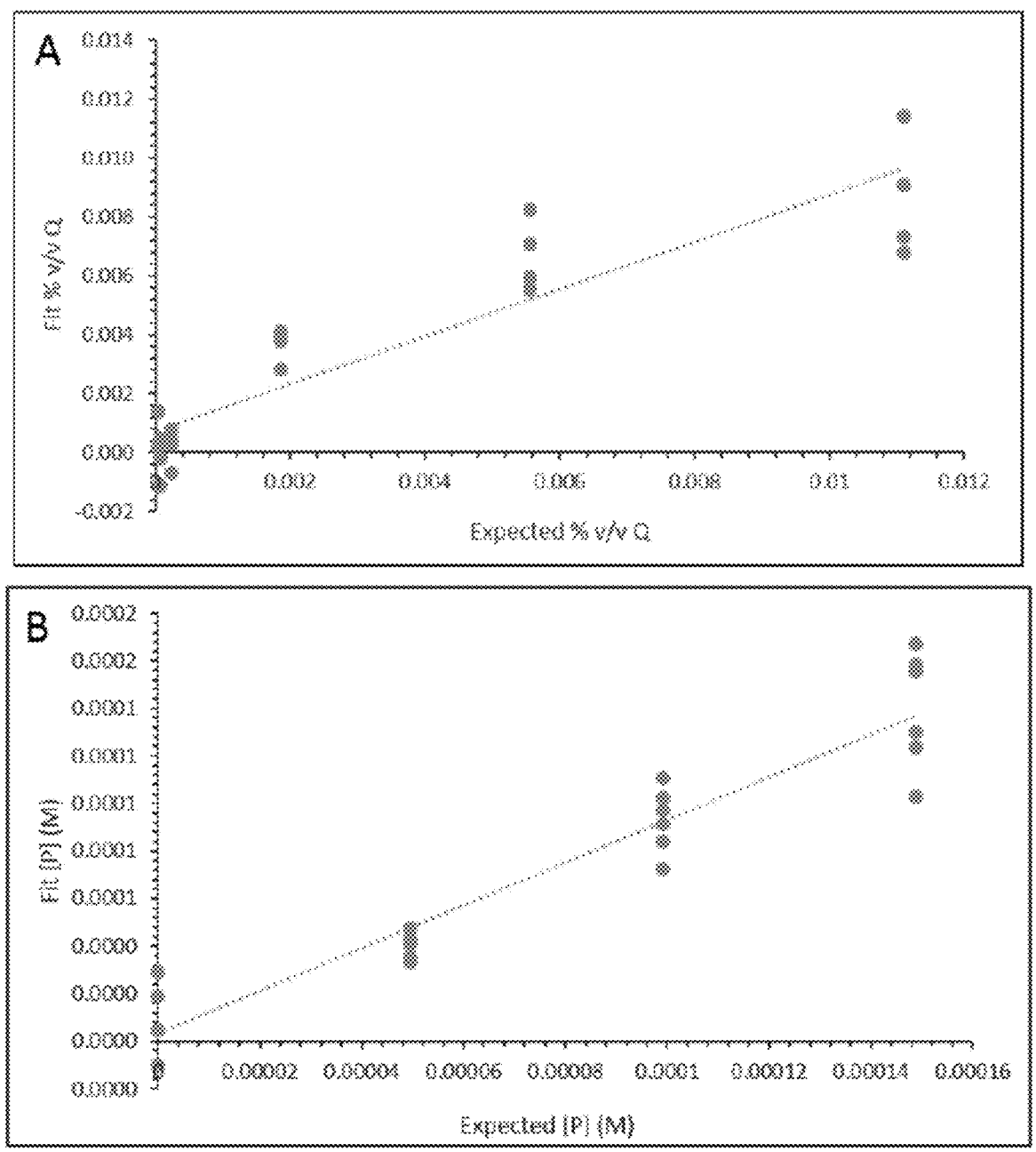
FIG. 6 is a series of graphs showing a comparison between the expected and the calculated values of A) $\phi_Q$ and B) [P]

The fit [P] and $\phi Q$ are compared to the expected values from FIGS. 2 and 3, presented in FIGS. 4-6. The calculated values of both [P] and $\phi Q$ match the experimental data very well at lower concentrations. However, the fit begins to deviate from linear behavior at higher concentrations of both porphyrin and quartz spheres consistent with the curvature in FIGS. 2B and 3B. This demonstrates that the higher concentrations are beginning to deviate from the linear regime. A more accurate fit could be refined if all of the concentrations stayed within the linear region.

Figure 7:
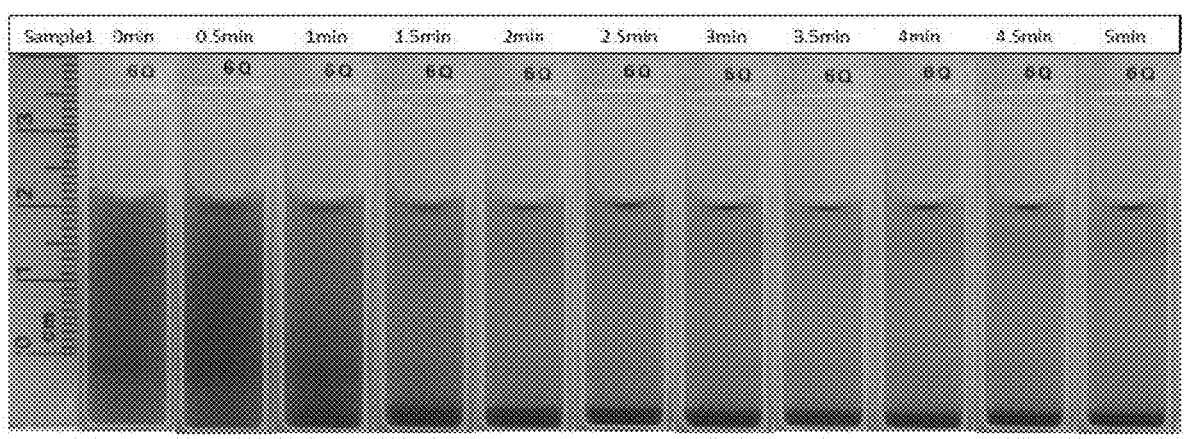
FIG. 7 is a series of images of quartz spheres settling with 0.0111% v/v spheres and 9.92E$^{-5}$M porphyrin'

A verification of the calculated parameters can be demonstrated by calculating the $\phi Q$ as the spheres settle out of the solution as a function of time. The hypothesis is that as the spheres settle out of the probed volume, the $\phi Q$ calculated by the algorithm will be decreasing. For reference, images of the sample cells over time are shown in FIGS. 7-9 demonstrating that the settling of the spheres can be visually observed. The recorded EE and IE are presented in FIG. 10 and the calculated $\phi Q$ and [P] in FIG. 11.

The volume fraction of quartz spheres is calculated to rapidly decrease at the start of the experiment then level off, which is visually observed in FIGS. 7-9. A greater initial concentration leads to quicker and more drastic changes from the settling. The result of increasing porphyrin concentration was initially surprising however, it is a logical outcome. In the overall sample it can be assumed that the porphyrin is equally dispersed throughout. Therefore, if the quartz spheres settle out of the probed volume, that volume experiences an increase in porphyrin containing solution giving an apparent rise in the porphyrin concentration. That is, the volume fraction increases in time as the porphyrin concentration is constant. Thus the model accurately and simultaneously represents the effect of changing concentrations and equal volumes as well as changing volumes with equal concentrations.

The turbidity of biological samples cause a distortion in the scattering, giving rise to a need for more accurate methods of measurement. The Hct algorithm presented above utilizes the measurement of both the inelastic and the elastic scattering intensities to approach the scattering distortion issue. The current work provides a validation of the algorithm by applying the same concept to an in vitro system that is analogous to the transcutaneous measurements. The measurement of EE and IE were linear with respect to both $\phi Q$ and [P] allowing for a bilinear fit providing the parameters a-f to fit the settling experiment. The results match what is expected affording support for the algorithm.

While the utility of this approach has been demonstrated, the experiments should be repeated within the linear regime for both EE and IE measurements. This data would give a more accurate and precise fit. Because there are many particle systems that are commercially available the present invention could be evaluated with other particles, such as polystyrene particles in aqueous glucose solution, to more thoroughly explore and probe this approach.

Algal biofuel production is a process that has received much attention as a more environmentally friendly renewable energy source. The present invention could be used to measure the growth of algae in a bulk solution before processing. A second application of the present application could be the determination of the viability of bacteria in a growing culture. The algae growth starts with proliferation where the cells multiply and ends with profusion by the production of fats which can be generated into biofuels. For these applications, the algae would be analogous to the RBCs, the nutrient solution would be analogous to plasma, and the background signal to contributions to in vivo optical probing EE and IE signals from the static tissue surrounding the intravascular space.

The algorithm of the present invention could thus be applied to the algae growth to measure both the proliferation and the profusion as a function of time. The advantage of this approach would be to measure the growth of the algae culture non-invasively instead of removing an aliquot which could potentially contaminate the culture.

The most advantageous time in which to start processing the grown algae could be anticipated granting maximum productivity. When inducing bacteria to produce a protein of interest, the growth of the culture can be measured by the change in optical density. While this is helpful to measure the growth, it would be favorable to measure the vitality of the bacteria. In this system, the bacteria would be analogous to the red blood cells, the liquid broth (LB) growth medium to plasma and the background signal to contributions to in vivo optical probing EE and IE signals from the static tissue surrounding the intravascular space. As live bacteria may be able to move throughout the solution, but dead bacteria would theoretically descend to the bottom at a constant rate. Thus, the example of the quartz spheres settling could be applied to a culture of bacteria to estimate the amount of dead bacteria. As the results from experiments utilizing a culture of bacteria can often take days to see the results, the present invention provides an ability to determine the liveliness of a culture while it is growing rather than realizing days later that the bacteria were not producing the protein.

The present invention may thus be used for fluorescence based immunoassays, nephalometry and turbidometry assays for biofluids, quantitative protein analysis, bioreactor design, process control, biofuel production, stem cell culturing, stem cell production and cell viability testing.

EXAMPLE

The following materials were used without further purification: Meso-tetra(4-Sulfonatophenyl) porphine dihydrochloride from Frontier Scientific, Cesium chloride from Sigma-Aldrich, SiO2 Microspheres, 8 vm from Cospheric, and Inorganic Membrane Filters, 0.02 vm 25 mm from Whatman. A 0.00496 M stock solution of Meso-tetra(4-Sulfonatophenyl) porphine dihydrochloride (porphyrin) was prepared by dissolving 50 mg in 10 mL of deionized (DI) water. A stock solution of cesium chloride was prepared by dissolving 12 g of CsCI in 20 mL of DI water to give a solution with a density of 1.6 g/mL. The solutions with quartz spheres were made in serial dilution. The first solution was prepared by adding 0.102 g quartz spheres to 5.1 mL of the stock CsCI solution to give a 0.02 g/mL solution. Dividing the 0.02 g/mL of quartz spheres by the density of 1.8 g/mL gives a % volume/volume (% v/v) of 0.0111 quartz spheres in solution for the most concentrated solution. This solution was used to make serial dilutions to solutions with volume fractions of $5.56E^{-3}$, $1.85E^{-3}$, $2.467E^4$, $8.22E^{-5}$, and 4.167E-5.

The Raman instrument uses a continuous wave external cavity laser operating at 785 nm (Process Instruments, Salt Lake, Utah). The laser delivers a maximum of 450 mW at the sample in a 1.5 cm$^{-1}$ spectral bandwidth within a multimode spatial distribution. The spot is roughly square and is focused to a spot about 125 mm wide at the sample. Spectra were collected with an exposure time of 0.02 seconds, accumulation time of 0.02 seconds and 1500 accumulations. The spectra of each sample was collected prior to porphyrin addition. Then, 30 µL of the stock 0.00496 M porphyrin solution was added to each solution, mixed thoroughly, and spectra were collected with an identical experimental setup. Following this same procedure, 30 µL of stock porphyrin was added then spectra were accumulated twice giving each quartz sphere sample at four different porphyrin concentrations: 0 M (OP), $4.96E^{-5}$ M (30P), $9.92E^{-5}$ M (60P), and $1.488E^{-4}$ M (90P). The raw data was transferred to Origin Lab 9.0 software for analysis.

For the settling experiment, the same porphyrin and CsCI stock solutions were used. Samples 1 and 3 were prepared with same 0.0111% v/v concentration as above and sample 2 was prepared with a 0.00185% v/v concentration. Samples 1 and 2 were given a $4.96E^{-5}$ M porphyrin concentration and sample 3 was given a $9.92E^{-5}$ M porphyrin concentration. The experimental setup was the same as for the previous experiment, however, there were 30 consecutive acquisitions for samples 1 and 3 and 40 acquisitions for sample 2 giving spectra every 30 seconds for 15 minutes and 20 minutes respectively.

What is claimed is:

1. A system for determining turbidity, comprising:
   a sample having a volume of a fluid and a plurality of particles suspended in the fluid;
   a laser aligned to direct light of a predetermined wavelength into the sample and cause an amount of emitted light having the predetermined wavelength and an amount of emitted light that has shifted to a second predetermined wavelength; and
   a detector aligned to simultaneously collect at least a portion of the amount of emitted light having the predetermined wavelength and at least a portion of the amount of emitted light that has shifted to the second predetermined wavelength and to simultaneously distinguish the amount of emitted light that has the predetermined wavelength and the amount of emitted light that has shifted to the second predetermined wavelength,
   wherein the detector is programmed to determine the turbidity based upon the relative intensity of emitted light having the predetermined wavelength that is collected by the detector and the intensity of emitted light that has shifted to the second predetermined wavelength that is collected by the detector, wherein the amount of emitted light having the predetermined wavelength that is collected by the detector represents the volume of the fluid, and wherein the amount of emitted light that has shifted to the second predetermined wavelength that is collected by the detector represents the plurality of particles suspended in the fluid.

2. The system of claim 1, wherein the predetermined wavelength is between 280-2500 nanometers.

3. The system of claim 2, wherein the detector is configured to measure 500-1800 $cm^{-1}$ for the shifted light and −30-+10 $cm^{-1}$ for the unshifted light.

4. The system of claim 3, wherein the predetermined wavelength is selected from the group consisting of 632, 405, 670, 450, 785, 805 and 830 nanometers.

5. The system of claim 4, wherein the in vitro sample comprises an algal biofuel solution.

6. The system of claim 4, wherein the in vitro sample comprises a growing culture of bacteria.

* * * * *